US011135119B2

(12) United States Patent
Sulzer et al.

(10) Patent No.: US 11,135,119 B2
(45) Date of Patent: Oct. 5, 2021

(54) ADAPTABLE ROBOTIC GAIT TRAINER

(71) Applicant: Board of Regents, The University of Texas System, Austin, TX (US)

(72) Inventors: James Sulzer, Austin, TX (US); Sung Yul Shin, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 411 days.

(21) Appl. No.: 15/958,106

(22) Filed: Apr. 20, 2018

(65) Prior Publication Data

US 2018/0303697 A1 Oct. 25, 2018

Related U.S. Application Data

(60) Provisional application No. 62/488,116, filed on Apr. 21, 2017.

(51) Int. Cl.
*A61H 1/02* (2006.01)
*A61H 3/00* (2006.01)
(Continued)

(52) U.S. Cl.
CPC ........... *A61H 1/0262* (2013.01); *A61H 1/024* (2013.01); *A61H 1/0237* (2013.01);
(Continued)

(58) Field of Classification Search
CPC ......... A61B 5/112; A61B 5/6829; A61H 1/00; A61H 1/024; A61H 1/0244; A61H 1/0262; A61H 1/0266; A61H 3/008; A61H 2201/0192; A61H 2201/1207; A61H 2201/1436; A61H 2201/1463; A61H 2201/1628; A61H 2201/163; A61H 2201/164; A61H 2201/1642; A61H 2201/50; A61H 2201/5043; A61H 2201/5064; A61H 2201/5079; A61H 2203/0487; A61H 2230/06; A61H 2230/40; A61H 2230/805; A63B 22/0235; A63B 21/4011; A63B 21/4013; A63B 2022/0038; A63B 2022/0043; A63B 2022/0033; B29J 9/0006
(Continued)

(56) References Cited

U.S. PATENT DOCUMENTS 7,803,125 B2 9/2010 Santos-Munne
8,308,618 B2 11/2012 Bayerlein
(Continued)

OTHER PUBLICATIONS

Garcia et al., "Design and evaluation of reconfigurable Klann mechanism based four legged walking robot", Dec. 2015, ResearchGate, pp. 1-6 (Year: 2015).*

(Continued)

*Primary Examiner* — Tu A Vo
*Assistant Examiner* — Alexander Morales
(74) *Attorney, Agent, or Firm* — Riverside Law LLP (57) ABSTRACT

A gait training system has a motor connected to a first linkage system by an actuator. The first linkage system has multiple linkage members connected to multiple joints and an endpoint that is configured to produce a cyclic gait motion when the motor is activated. First and second linkage members have an adjustable length. A method of customizing a gait pattern on a gait training system is also described.

13 Claims, 9 Drawing Sheets

(51) Int. Cl.
    A61B 5/11      (2006.01)
    A63B 22/02     (2006.01)
    A61B 5/00      (2006.01)
    B25J 9/00      (2006.01)
(52) U.S. Cl.
    CPC ......... *A61H 1/0244* (2013.01); *A61H 1/0255* (2013.01); *A61H 3/008* (2013.01); *B25J 9/0006* (2013.01); *A61B 5/112* (2013.01); *A61B 5/6829* (2013.01); *A61H 2201/1436* (2013.01); *A61H 2201/163* (2013.01); *A61H 2201/1642* (2013.01); *A61H 2230/06* (2013.01); *A61H 2230/40* (2013.01); *A63B 22/0235* (2013.01)
(58) Field of Classification Search
    USPC .......... 601/23–33, 31–35; 482/57, 62–64, 66
    See application file for complete search history.

(56) References Cited

U.S. PATENT DOCUMENTS

| | | | |
|---|---|---|---|
| 8,920,347 B2 | 12/2014 | Bayerlein | |
| 2008/0249438 A1 | 10/2008 | Agrawal | |
| 2008/0255488 A1* | 10/2008 | Agrawal | A63B 69/0064 602/23 |
| 2008/0304935 A1* | 12/2008 | Scott | A61H 1/0262 414/5 |
| 2010/0270771 A1* | 10/2010 | Kobayashi | A61H 1/0255 280/210 |
| 2011/0071442 A1* | 3/2011 | Park | A61B 5/112 601/35 |
| 2013/0226048 A1 | 8/2013 | Unluhisarcikli | |
| 2014/0087922 A1* | 3/2014 | Bayerlein | A63B 21/00181 482/54 |
| 2015/0297934 A1* | 10/2015 | Agrawal | A63B 21/4025 482/4 |
| 2016/0016309 A1* | 1/2016 | Swift | B25J 9/0006 623/24 |
| 2017/0080559 A1* | 3/2017 | Namoun | B25J 9/06 |
| 2017/0281999 A1* | 10/2017 | Lilley | A63B 22/02 |
| 2018/0071580 A1* | 3/2018 | Lee | A61H 3/00 |

OTHER PUBLICATIONS

Nansai et al., "On a Jansen leg with multiple gait patterns for reconfigurable walking platforms", Jan. 2015, SAGE, pp. 1-18 (Year: 2015).*

Tsuje et al., "Synthesis of a 10-bar linkage to guide the gait cycle of the human leg", Aug. 2, 2015, U.C. Irvine, pp. 1-8 (Year: 2015).*

Tsuje et al., "An adjustable single degree-of-freedom system to guide natural walking movement for rehabilitation", Dec. 1, 2016, U.C. Irvine, pp. 1-9 (Year: 2016).*

Jansen, B., E. L. Doubrovski, and J. C. Verlinden, Animaris Geneticus Parvus: Design of a complex multi-body walking mechanism. Rapid Prototyping Journal, 2014. 20(4): p. 311-319.

H. Vardhan, A. KSSK, P. Kotaru, S. Srinivasan, Assistive exercise mechanism for people with lower limb disabilities, ME6710, Theory of Mechanism Project, Indian Institute of Technology Madras, 2013, 14 pages.

Hesse and Uhlenbrock, 2000, "A mechanized gait trainer for restoration of gait." J Rehabil Res Dev. 37(6): 701-708.

Colombo et al., 2000, "Treadmill training of paraplegic patients using robotic orthosis." J Rehabil Res Dev. 37(6): 693-700.

Emken et al., 2006, "A robotic device for manipulating human stepping." IEEE Transactions on Robotics. 22(1): 185-189.

Veneman et al., 2007 "Design and evaluation of the LOPES exoskeleton robot for interactive gait rehabilitation." IEEE Trans Neural Syst Rehabil Eng. 15(3): 379-386.

Banala et al., 2006, "Gravity-Balancing Leg Orthosis and Its Performance Evaluation." IEEE Transactions on Robotics. 22(6): 1228-1239.

Peshkin et al., 2005 "KineAssist: A robotic overground gait and balance training device." 9th International Conference on Rehabilitation Robotics, 7 pages.

Kawamoto et al., 2009, "Development of single leg version of HAL for hemiplegia." Conf Proc IEEE Eng Med Biol Soc.: 5038-5043.

Galvez and Reinkensmeyer, 2005, "Robotics for Gait Training After Spinal Cord Injury." Topics in Spinal Cord Injury Rehabilitation. 11(2): 18-33.

Zeilig et al. 2012, "Safety and tolerance of the ReWalk™ exoskeleton suit for ambulation by people with complete spinal cord injury: a pilot study." J Spinal Cord Med. 35(2): 96-101.

Wu et al., 2011, "A cable-driven locomotor training system for restoration of gait in human SCI." Gait Posture, 33(2): 256-260.

Ha et al., 2012, "Enhancing stance phase propulsion during level walking by combining FES with a powered exoskeleton for persons with paraplegia." Conf Proc IEEE Eng Med Biol Soc, 344-347.

Mehrholz and Pohl, 2012, "Electromechanical-assisted gait training after stroke: a systematic review comparing end-effector and exoskeleton devices." J Rehabil Med, 44(3): 193-199.

Zoss et al., 2006, "Biomechanical Design of the Berkeley Lower Extremity Exoskeleton (BLEEX)." IEEE/ASME Transactions on Mechatronics. 11(2): 128-138.

Jung et al., 2014, "Design and control of an exoskeleton system for gait rehabilitation capable of natural pelvic movement." 2014 IEEE/RSJ International Conference on Intelligent Robots and Systems., 6 pages.

Siddharth, 2015, "Design and Analysis of a 1-DOF Walking Mechanism." www.siddharthswaminathan.in/files/WalkingMechanism )(accessed Jul. 22, 2015), 7 pages.

Jørgensen et al., 1995, "Recovery of Walking Function in Stroke Patients: The Copenhagen Stroke Study," Arch. Phys. Med. Rehabil., 76:27-32.

Wyndaele et al., 2006, "Incidence, Prevalence and Epidemiology of Spinal Cord Injury: What Learns a Worldwide Literature Survey?," Spinal Cord, 44:523-529.

Kwakkel et al., 2006, "Impact of Time on Improvement of Outcome after Stroke," Stroke, 37:2348-2353.

Camicia et al., 2016, "Length of Stay at Inpatient Rehabilitation Facility and Stroke Patient Outcomes," Rehabil. Nurs., 41(2), pp. 78-90.

Van Peppen et al., 2004, "The Impact of Physical Therapy on Functional Outcomes after Stroke: What's the Evidence?," Clin. Rehabil., 18(8), pp. 833-862.

Cramer et al., 2008, "Neuroplasticity and Brain Repair after Stroke," Curr. Opin. Neurol., 21(1), pp. 76-82.

Riener R, 2016, "Technology of the Robotic Gait Orthosis Lokomat," Neurorehabilitation Technology, Second Edition, Springer International Publishing, pp. 395-407.

Mehrholz et al., 2017, "Electromechanical-Assisted Training for Walking after Stroke," Cochrane Database Syst. Rev., 2017(5), 128 pages.

Nam et al., 2017, "Robot-Assisted Gait Training (Lokomat) Improves Walking Function and Activity in People with Spinal Cord Injury: A Systematic Review," J. NeuroEngineering Rehabil., 14(1), p. 24.

Hesse et al., 2001, "An Electromechanical Gait Trainer for Restoration of Gait in Hemiparetic Stroke Patients: Preliminary Results," Neurorehabil. Neural Repair, 15(1), pp. 39-50.

Smania et al., 2018, "The End-Effector Device for Gait Rehabilitation," Advanced Technologies for the Rehabilitation of Gait and Balance Disorders, G. Sandrini, V. Homberg, L. Saltuari, N. Smania, and A. Pedrocchi, eds., Springer International Publishing, Cham, pp. 267-283.

Dietz V, 2002, "Proprioception and Locomotor Disorders," Nat. Rev. Neurosci., 3(10), pp. 781-790.

Ji et al., 2008, "Synthesis of a Pattern Generation Mechanism for Gait Rehabilitation," J. Med. Devices Trans. ASME, 2(3), 8 pages.

Kora et al., 2017, "Design, Analysis, and Optimization of an Acute Stroke Gait Rehabilitation Device," J. Med. Devices Trans. ASME, 11(1), 6 pages.

Tsuge et al., 2016, "An Adjustable Single Degree-of-Freedom System to Guide Natural Walking Movement for Rehabilitation," J. Med. Devices Trans. ASME, 10(4), 6 pages.

(56) References Cited

OTHER PUBLICATIONS

Tsuge et al., 2016, "Homotopy Directed Optimization to Design a Six-Bar Linkage for a Lower Limb with a Natural Ankle Trajectory," J. Mech. Robot., 8(6), pp. 1-7.
Shao et al., 2016, "Conceptual Design and Dimensional Synthesis of Cam-Linkage Mechanisms for Gait Rehabilitation," Mech. Mach. Theory, 104, pp. 31-42.
Wang et al., 2009, "Design and Control of an Active Gait Trainer," IEEE International Symposium on Industrial Electronics, pp. 1779-1784.
Tsuge et al., 2015, "Synthesis of a 10-Bar Linkage to Guide the Gait Cycle of the Human Leg," Proceedings of the ASME Design Engineering Technical Conference, American Society of Mechanical Engineers, 8 pages.
Yul Shin et al., 2018, "Design of a Single Degree-of-Freedom, Adaptable Electromechanical Gait Trainer for People With Neurological Injury," J. Mech. Robot., 10(4), p. 044503.
Sabaapour et al., 2019, "Development of a Novel Gait Rehabilitation Device with Hip Interaction and a Single DOF Mechanism," 2019 International Conference on Robotics and Automation (ICRA), pp. 1492-1498.
Haghjoo et al., 2020, "Mech-Walker: A Novel Single-DOF Linkage Device with Movable-Frame for Gait Rehabilitation," IEEEASME Trans. Mechatron., pp. 1-1.
Yun, Y et al., 2014, "Statistical Method for Prediction of Gait Kinematics with Gaussian Process Regression," J. Biomech., 47(1), pp. 186-192.
Koopman, B., van Asseldonk, E. H. F., and Van der Kooij, H., 2014, "Speed-Dependent Reference Joint Trajectory Generation for Robotic Gait Support," J. Biomech., 47(6), pp. 1447-1458.
Shin, S. Y., and Sulzer, J., 2019, "An Online Transition of Speed-Dependent Reference Joint Trajectories for Robotic Gait Training," 2019 IEEE 16th International Conference on Rehabilitation Robotics (ICORR), pp. 983-987.
Norton, R., 2004, Design of Machinery: An Introduction to the Synthesis and Analysis of Mechanisms and Machines, McGraw-Hill Education, New York, 924 pages.
Ullah, I., and Kota, S., 1997, "Optimal Synthesis of Mechanisms for Path Generation Using Fourier Descriptors and Global Search Methods," J. Mech. Des., 119(4), pp. 504-510.
Cunningham, D. A., Rechnitzer, P. A., Pearce, M. E., and Donner, A. P., 1982, "Determinants of Self-Selected Walking Pace across Ages 19 to 66," J. Gerontol., 37(5), pp. 560-564.
Yang, J., and Li, Z., 2010, "A Novel Contour Error Estimation for Position Loop-Based Cross-Coupled Control," IEEEASME Trans. Mechatron., 16(4), pp. 643-655.
Haimes, Y., 1971, "On a Bicriterion Formulation of the Problems of Integrated System Identification and System Optimization," IEEE Trans. Syst. Man Cybern., 1(3), pp. 296-297.
Laumanns, M., Thiele, L., and Zitzler, E., 2005, "An Adaptive Scheme to Generate the Pareto Front Based on the Epsilon-Constraint Method," Practical Approaches to Multi-Objective Optimization, J. Branke, K. Deb, K. Miettinen, and R.E. Steuer, eds., Internationales Begegnungs- und Forschungszentrum für Informatik (IBFI), Schloss Dagstuhl, Germany, Dagstuhl, Germany, 11 pages.
Gill, P. E., Murray, W., and Wright, M. H., 1981, Practical Optimization, Academic Press, London, 421 pages.
Powell, M. J. D., 1983, "Variable Metric Methods for Constrained Optimization," Mathematical Programming The State of the Art, Springer Berlin Heidelberg, pp. 288-311.
Stone, M., 1974, "Cross-Validatory Choice and Assessment of Statistical Predictions," J. R. Stat. Soc. Ser. B Methodol., 36(2), pp. 111-133.
Hastie, T., Tibshirani, R., and Friedman, J., 2009, The Elements of Statistical Learning: Data Mining, Inference, and Prediction, Springer Science & Business Media, 764 pages.
Winter, D. A., 2009, Biomechanics and Motor Control of Human Movement: Fourth Edition, 383 pages.
McCulloch, 2003, Generalized Linear Mixed Models (Beachwood OH: Institute of Mathematical Sciences; Alexandria VA: American Statistical Association), 28-33.
Freivogel, S., Mehrholz, J., Husak-Sotomayor, T., and Schmalohr, D., 2008, "Gait Training with the Newly Developed 'LokoHelp'-System Is Feasible for Non-Ambulatory Patients after Stroke, Spinal Cord and Brain Injury. A Feasibility Study," Brain Inj., 22(7-8), pp. 625-632.
Fukuchi, C. A., Fukuchi, R. K., and Duarte, M., 2019, "Effects of Walking Speed on Gait Biomechanics in Healthy Participants: A Systematic Review and Meta-Analysis," Syst. Rev., 8(1), 11 pages.
Nielsen, J. B., Crone, C., and Hultborn, H., 2007, "The Spinal Pathophysiology of Spasticity—From a Basic Science Point of View," Acta Physiologica, pp. 171-180.
Jones, T. A., 2017, "Motor Compensation and Its Effects on Neural Reorganization after Stroke," Nat. Rev. Neurosci., 18(5), pp. 267-280.
Dietz, V., Colombo, G., and Jensen, L., 1994, "Locomotor Activity in Spinal Man," The Lancet, 344(8932), pp. 1260-1263.
Ghosh, S., Robson, N., and McCarthy, J. M., 2020, "Kinematic Design and Evaluation of a Six-Bar Knee-Ankle-Foot Orthosis," J. Eng. Sci. Med. Diagn. Ther., 3(2), 9 pages.
McKendry, J., Brown, B., Westervelt, E. R., and Schmiedeler, J. P., 2007, "Kinematic Design and Dynamic Analysis of a Planar Biped Robot Mechanically Coordinated by a Single Degree of Freedom," Proceedings—IEEE International Conference on Robotics and Automation, pp. 1875-1880.
Al-Araidah, O., Batayneh, W., Darabseh, T., and BaniHani, S. M., 2011, "Conceptual Design of a Single DOF Human-like Eight-Bar Leg Mechanism," Jordan J. Mech. Ind. Eng., 5(4), pp. 285-289.
Zhao, P., Zhu, L., Zi, B., and Li, X., 2019, "Design of Planar 1-DOF Cam-Linkages for Lower-Limb Rehabilitation via Kinematic-Mapping Motion Synthesis Framework," J. Mech. Robot., 11(4).

\* cited by examiner

ADAPTABLE ROBOTIC GAIT TRAINER

CROSS-REFERENCE TO RELATED APPLICATIONS

This application claims priority to U.S. provisional application No. 62/488,116 filed on Apr. 21, 2017 and incorporated herein by reference in its entirety.

BACKGROUND OF THE INVENTION

Walking is a gait of locomotion among legged animals, including humans. It is a complex motion, with actuation of muscles and nerves, and modeling this motion has been the focus of numerous researchers over the years. Research areas range from developing intelligent control mechanisms to biologically inspired walking mechanisms for various terrains. Research into the mechanism of walking has led to different types of exoskeletons and orthotic devices to assist human motion. Applications for these devices include augmenting of muscular force of healthy subjects and rehabilitation of people with motion impairments.

Gait impairment following neurological injury is common. For people with neurological impairments after a spinal cord injury or a stroke, electromechanical, or robotic, gait trainers have shown significant functional benefits. These devices carry the limbs through a natural gait trajectory and induce ground contact forces, important for sensorimotor recovery. Benefits also include improvement in walking independence and mobility, functional walking ability, gait speed, muscle activation and joint range of motion. Recent meta-analyses on robotic gait training also concluded that it improves the chance of achieving independent walking and locomotor ability after stroke and spinal cord injury patients. However, conventional robotic gait trainers are complex and are often prohibitively expensive. For instance, the most commercially successful robotic trainers utilize multiple actuators that require multiple motors and sophisticated control algorithms. These systems can cost up to 20% or more of a large hospital's annual capital expenditures. The high cost of these complex conventional systems makes them unaffordable for many healthcare facilities. These complex systems also require complex systems and methods for adjusting gait patterns to fit the patient's needs.

Thus, there is a need in the art for an improved and simplified robotic gait trainer that can operate without sacrificing the therapeutic benefits of locomotor training and can cover a large range of gait patterns.

SUMMARY OF THE INVENTION

In one embodiment, a gait training system includes a motor connected to a first linkage system by an actuator, where the first linkage system includes multiple linkage members connected to multiple joints and an endpoint that is configured to produce a cyclic gait motion when the motor is activated, and where first and second linkage members of the multiple linkage members have an adjustable length. In one embodiment, the endpoint is located at a bottom joint of the first linkage system. In one embodiment, the system includes an ankle cuff attached to the bottom joint. In one embodiment, the system includes an extension linkage attaching the ankle cuff to the bottom joint. In one embodiment, the first and second linkage members are connected to a common joint. In one embodiment, the first linkage system comprises 12 linkage members. In one embodiment, the first linkage system comprises 8 joints. In one embodiment, the endpoint can be configured to produce at least 9 different cyclic gait motions by adjusting a length of at least one of the first and second linkage members. In one embodiment, the actuator comprises a drive belt. In one embodiment, the actuator is connected to a second linkage system. In one embodiment, the system includes a second linkage system comprising a second plurality of linkage members connected to a second plurality of joints and a second endpoint that is configured to produce a cyclic gait motion 180 degrees out of phase with the first endpoint when the motor is activated. In one embodiment, a first and second linkage members of the second plurality of linkage members have an adjustable length. In one embodiment, the system includes a treadmill disposed below the first linkage system. In one embodiment, the system includes a sensor configured to detect a measure of at least one of user weight or movement and provide a feedback signal to the treadmill for controlling a speed of the treadmill. In one embodiment, the system includes a body weight support system connected to a rail disposed above the first linkage system. A method of customizing a gait pattern on a gait training system includes the steps of providing the gait training system, and adjusting the length of at least one of the first and second linkage members to correspond with a first gait pattern. In one embodiment, the method includes the step of after to the step of adjusting, readjusting the length of at least one of the first and second linkage members to correspond with a second gait pattern that is different than the first gait pattern.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

It is to be understood that the figures and descriptions of the present invention have been simplified to illustrate elements that are relevant for a more clear comprehension of the present invention, while eliminating, for the purpose of clarity, many other elements found in robotic gait training systems. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is an adaptable robotic gait training system.

A simplified and low cost robotic gait trainer is disclosed that can be operated without sacrificing therapeutic benefits of locomotor training. Instead of using multiple motors and actuators as is the case with conventional robotic gait training device, embodiments of the invention use a single motor and a single actuator to produce a natural cyclic gait motion. This single-actuated bilateral gait trainer can cover a large range of gait patterns by adjustment of as few as two links. Embodiments of the invention are simplified and can be manufactured at a low cost compared to conventional gait trainers, making the disclosed gait trainer accessible to a whole new market including resource-limited hospitals, outpatient clinics, patient homecare settings and research labs. Embodiments of the invention maintain functional benefits including a natural walking pattern and ground contact while also covering a large range of gait patterns using as few as two link adjustments.

Figure 1A:
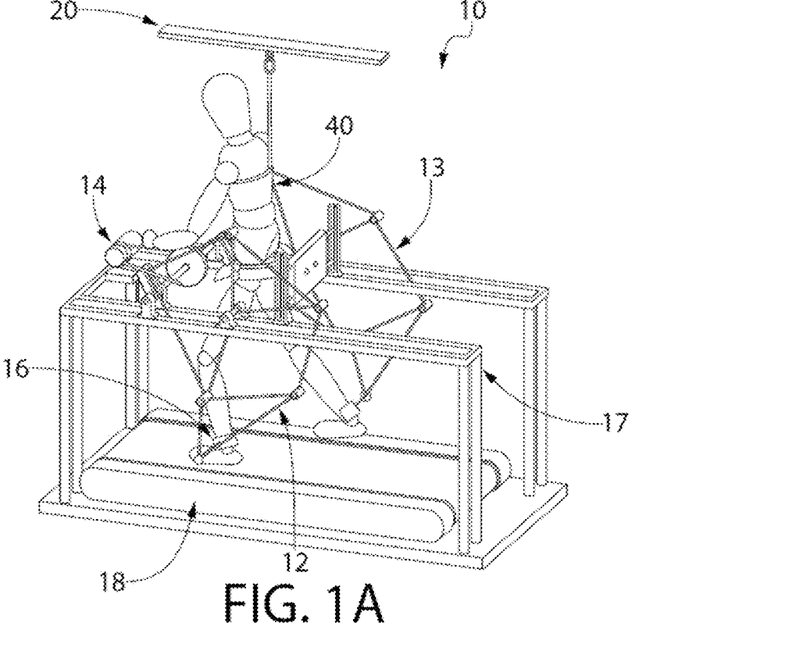
FIG. 1A is a perspective view and FIG. 1B is a side view of a gait training system according to one embodiment.
Figure 1B:
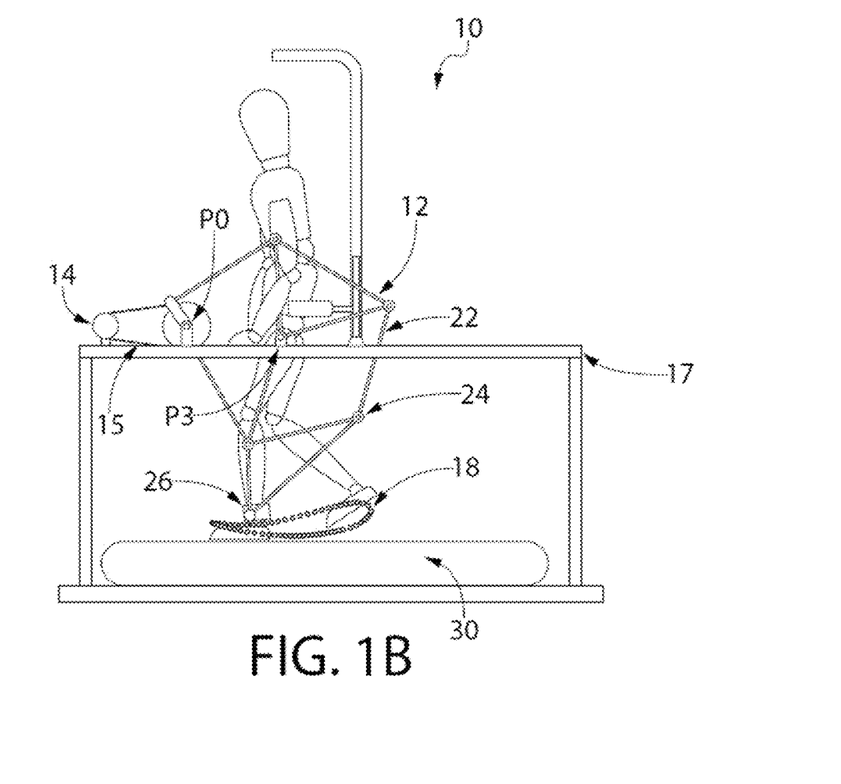

With reference now to FIGS. 1A and 1B, a gait trainer system 10 is shown according to one embodiment. The gait trainer 10 includes a linkage system 12, 13 that is powered by actuator mechanism 15 such as a motor 14 driven belt and pulley system connected to a first 12 and second 13 linkage system. Certain embodiments of the gait trainer 10 may only include a single linkage system 12, such as when the system is only required to be connected to a single ankle. The first linkage system 12 for example includes multiple linkage members 22 connected at a number of rotational joints 24. An endpoint rotational joint 26 is configured to produce a cyclic gait motion 30 when the motor 14 is activated. In one embodiment, the endpoint 26 is located at a bottom joint of the first linkage system 12. In one embodiment, an ankle cuff 16 is attached to the bottom joint. At least two linkage members 22 have an adjustable length. A treadmill 18 is positioned below the linkage systems for the user to walk on, and a body weight support system 40 is connected to a rail 20 disposed above the linkage systems. In certain embodiments, a frame 17 that is either integral to, connected to, or separate from the treadmill 18 is used to support at least one of the linkage systems 12, 13, the motor 14 and the actuator 15.

By using a crank mechanism with 180 degree phase shift as an actuator 15 connected to the motor 14, the gait trainer 10 can be operated bilaterally by using a single motor 14. In one embodiment, the actuator includes a drive belt and a pulley. In one embodiment, the actuator 15 is connected only to a single linkage system. In another embodiment, the actuator 15 is connected to two linkage systems. In one embodiment, each link is composed of an aluminum tube with two revolute joints at both ends. In one embodiment, the links can be composed of carbon fiber or other lightweight material. In one embodiment, rotary bearings can be used to reduce frictions at joints. In one embodiment, adjustable linkages can use two aluminum cylindrical tubes telescoped with a tube clamp that can be set by hand when the device is not in motion. In one embodiment, the link length adjustment can be made using threaded rods. In one embodiment, the adjustment can be made using motorized rods.

In certain embodiments, particular joints can move during gait locomotion whereas other joints may remain stationary. As shown in FIGS. 1A and 1B with additional reference to FIG. 2A, in one embodiment, joints $P_0$ and $P_3$ are stationary and fixed to the frame 17. The remaining joints in this example move as the linkage system moves through gait locomotion. Thus, in certain embodiments, particular links (such as in this example $L_4$) are formed by a separate structure, such as the stationary treadmill frame. The length of link $L_4$ can be adjusted by changing for example where joints $P_0$ or $P_3$ are attached to the treadmill frame. In some embodiments, one or both of $P_0$ and $P_3$ can be slidably positioned and locked into place along the horizontal length of treadmill frame 17. Moving $P_0$ and $P_3$ further apart on the frame 17 will lengthen $L_4$, whereas mounting $P_0$ and $P_3$ closer together on the frame 17 will shorten $L_4$. It should thus be appreciated that $L_4$ may be a lightweight tube, a portion of frame 17, or it may simply be a distance between joints $P_0$ and $P_3$. In certain embodiments, the linkage system is formed by links that include a combination of adjustable, non-adjustable, stationary and moving links 22. In certain embodiments, at least some of the joints 24 of the linkage system 12, 13 are stationary and mounted on a separate apparatus for suspending the linkage system over a walking system such as a treadmill.

Advantageously, the gait trainer 10 can produce subject-specific gait patterns by adjusting link lengths. Human gait movements possess inherent variability and change with body features such as age, gender, height or gait speed. The embodiments described herein can easily adjust for variations in gait kinematics by adjusting at least two link lengths. Link lengths can be adjusted by a number of methods, including but not limited to switching out links of different lengths, using a telescoping mechanism to change link lengths, using a screw mechanism to change link lengths, adding or stacking on (or removing) spacers or additional link segments to change link lengths, indexed link lengths, motorized adjustments, or using any other technique for lengthening a link segment as might be apparent to those having ordinary skill in the art. In one embodiment, the first linkage system includes 12 linkage members. In other embodiments, the first linkage system includes 10 or 11 linkage members. In one embodiment, the first linkage system includes 8 joints. In one embodiment, the endpoint 26 can be configured to produce at least 9 different cyclic gait motions by adjusting a length of at least two linkage members. In other embodiments, the endpoint 26 can be configured to produce at least 9 different cyclic gait motions by adjusting a length of only one or only two linkage members.

To accommodate the human subject training on the device, in one embodiment, parameters such as body weight support and movement of the ankle cuff are monitored by sensors as feedback for the treadmill speed. In one embodiment during gait training, the interaction force between the human and device is monitored. In one embodiment, the linkage system is manufactured from an appropriate material such as aluminum to make the device sturdy enough to overcome the interaction force exerted by the human subject, but yet smart enough to guarantee the safety by detecting motion intent and interaction forces using a sensorized cuff. Synchronization between the treadmill and the mechanism will be controlled to enable the subjects to safely train the gait on the device.

In one embodiment, the system may provide software applications accessible to one or more users, such as the user being evaluated and a medical professional, to perform one or more functions or provide system or user feedback. Such applications may be available at the same location as the user, or at a location remote from the user, such as via a local or remote display. A controller can also be connected to sensors and electromechanical components associated with the system for indicating user performance and system function, and for sending control signals to the components. A graphical user interface (GUI) can be implemented for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. The GUI may display for example gait patterns, system speeds, system performance, and may also include physiological feedback from body sensors, such as heartrate and breathing patterns.

Figure 2A:
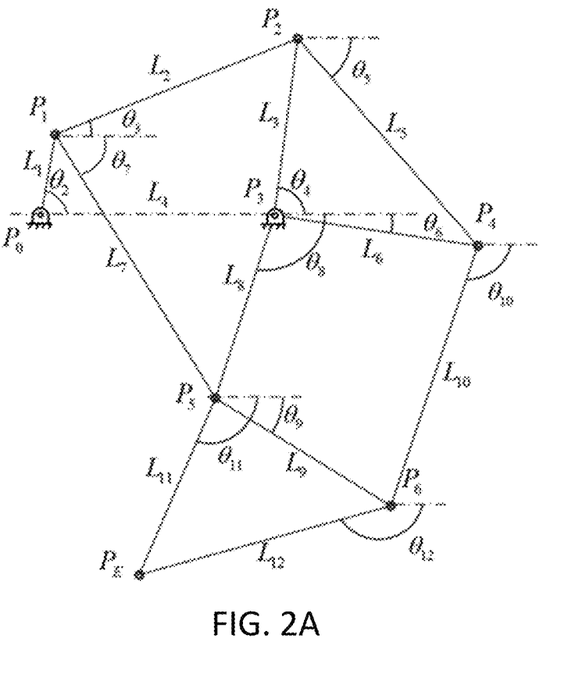
FIG. 2A is a diagram of a first linkage system according to one embodiment.
Figure 2B:
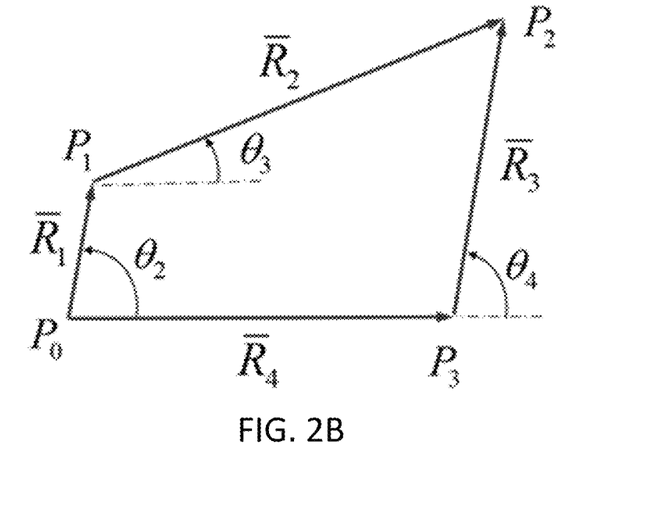
FIG. 2B is a diagram of a vector loop applied around the upper four-bar mechanism, $L_1L_2L_3L_4$.

Reproducing gait patterns from the perspective of the ankle requires a complex kinematic mechanism. With reference now to FIG. 2A, the linkage system according to one embodiment uses 8 moving linkages parameterized in 12 different lengths comprising four closed loop components; a pair of upper and lower four-bar mechanisms, $L_1L_2L_3L_4$ and $L_1L_7L_8L_4$, respectively, a coupler, $L_3L_5L_6$, a parallelogram mechanism, $L_6L_8L_9L_{10}$ and a rigid foot-link, $L_9L_{11}L_{12}$. In the application of a gait trainer, the main interest is the end-point at the rigid foot-link, $P_E$, the ankle interface (see e.g. FIG. 1A). Motion at $P_E$ can be determined by the configuration of the mechanism with the input angle of the rotary crank, $\theta_2$ expressed as $$P_E = f(\theta_2, \ldots \theta_{12}, l_1, \ldots, l_{12}), \tag{1}$$

where $\theta_i$ is the unknown $i^{th}$ joint angle (i=3, ..., 12) and $l_i$ is the given length of $i^{th}$ link. The vector loop representation, widely used for the motion analysis of mechanisms, solves for unknown parameters by creating a vector loop (or loops) around the linkages of the mechanism. As shown in FIG. 2A, the mechanism can be separated into four components; a pair of upper and lower four-bar mechanisms, $L_1L_2L_3L_4$ and $L_1L_7L_8L_4$, respectively, a coupler, $L_3L_5L_6$, a parallelogram mechanism, $L_6L_8L_9L_{10}$ and a rigid foot-link, $L_9L_{11}L_{12}$. The vector loop can be applied to each component to find all the unknowns that are necessary to define the configuration of the mechanism. One can first start with the upper four-bar mechanism, $L_1L_2L_3L_4$ to solve for the unknowns. The vector loop applied around the upper four-bar mechanism, $L_1L_2L_3L_4$ is shown in FIG. 2B. The vector loop equation is given by $$\overline{R}_1 + \overline{R}_2 - \overline{R}_3 - \overline{R}_4 = \overline{0} \tag{2}$$

where $\overline{R}_i$ represents the position vector applied on the $i^{th}$ link. By substituting the complex number notation for each position vector, the vector loop equation becomes $$l_1 e^{j\theta_2} + l_2 e^{j\theta_3} - l_3 e^{j\theta_4} - l_4 e^{j\theta_1} = 0. \tag{3}$$

Using the Euler identity, the vector loop equation can be expressed by $$l_1(\cos\theta_2 + j\sin\theta_2) + l_2(\cos\theta_3 + j\sin\theta_3) - l_3(\cos\theta_4 + j\sin\theta_4) - l_4 = 0 \tag{4}$$

with $\theta_1 = 0$. This equation can be now separated into its real and imaginary parts and each set to zero. By using the given input angle of the rotary crank, $\theta_2$ with the link lengths, $l_1, \ldots, l_4$, the two unknown angles, $\theta_3$ and $\theta_4$ can be solved with the real part $$l_1 \cos\theta_2 + l_2 \cos\theta_3 - l_3 \cos\theta_4 - l_4 = \overline{0} \tag{5}$$

and the imaginary part $$l_1 \sin\theta_2 + l_2 \sin\theta_3 - l_3 \sin\theta_4 = \overline{0} \tag{6}$$

of the vector loop equation. By using the two equations, the solution for the unknown angles are $$\theta_4 = 2\tan^{-1}\left(\frac{-B \pm \sqrt{B^2 - 4AC}}{2A}\right); \tag{7}$$

$$\theta_3 = 2\tan^{-1}\left(\frac{-B \pm \sqrt{B^2 - 4DE}}{2D}\right) \text{ where}$$

$$A = -\frac{l_4}{l_1} - \frac{l_4}{l_3}\cos\theta_2 + \frac{l_1^2 - l_2^2 + l_3^2 + l_4^2}{2l_1 l_3} + \cos\theta_2 \tag{8}$$

$$B = -2\sin\theta_2 \tag{9}$$

$$C = \frac{l_4}{l_1} - \left(\frac{l_4}{l_3} + 1\right)\cos\theta_2 + \frac{l_1^2 - l_2^2 + l_3^2 + l_4^2}{2l_1 l_3} \tag{10}$$

$$D = -\frac{l_4}{l_1} + \frac{l_4}{l_2}\cos\theta_2 + \frac{l_3^2 - l_1^2 - l_2^2 - l_4^2}{2l_1 l_2} + \cos\theta_2 \tag{11}$$

$$E = \frac{l_4}{l_1} - \left(\frac{l_4}{l_2} - 1\right)\cos\theta_2 + \frac{l_3^2 - l_1^2 - l_2^2 - l_4^2}{2l_1 l_2} \tag{12}$$

Note that the unknown angles have two solutions, obtained from the ±conditions on the radical. As with any quadratic equation, these two solutions may be of three types: real and equal, real and unequal, and complex conjugate. If the discriminant under the radical is negative, then the solution is complex conjugate, which simply means that the given link lengths are not physically capable of connection for the input angle, $\theta_2$. Excepting this situation, the solution will usually be real and unequal, meaning that there are two values of unknown angles corresponding to any one value of $\theta_2$. These are referred to as the open and crossed configurations of the four-bar linkage mechanism. Either solution can be easily selected based on the configuration of the mechanism. The unknowns of the four-bar mechanism can be solved for by using the vector loop representation. Similarly, the rest of the unknown angles ($\theta_5, \ldots, \theta_{12}$) can be solved by expanding these vector loops around the other components and then all the joint positions and the end-point can be calculated with the input angle, $\theta_2$. With the input angle, $\theta_2$ given at every instant, the end-point path can be determined by the unknowns solved with the vector loop equations.

Human gait patterns can be recreated while minimizing of the number of adjustable linkages that can reproduce these pattern. In the model, the cost function of the mechanism configuration based on the meta-trajectory is formulated as $$\min_L \cdot J(L) = \frac{1}{2} \sum_{k=1}^{f} \{p_H(t_k) - p_E(\tau_k, L)\}^2 + \|A_H - A_E\| \tag{13}$$

such that $L_{Lower} \leq L \leq L_{upper}$ where $p_H$ is the reference meta-trajectory, $p_E$ is the end-point trajectory of the linkage mechanism, $A_H$ and $A_E$ are the area of gait patterns of meta-trajectory and end-point trajectory in sagittal plane, respectively, L is a link length vector that incorporates all 12 lengths of the mechanism, $t_k$ is the $k^{th}$ time frame and $\tau_k$ is the $k^{th}$ time frame that minimizes the error between $p_H$ and $p_E$. $L_{Lower}$ and $L_{Upper}$ are lower and upper boundary condition vector of the link lengths, respectively.

Figure 2C:
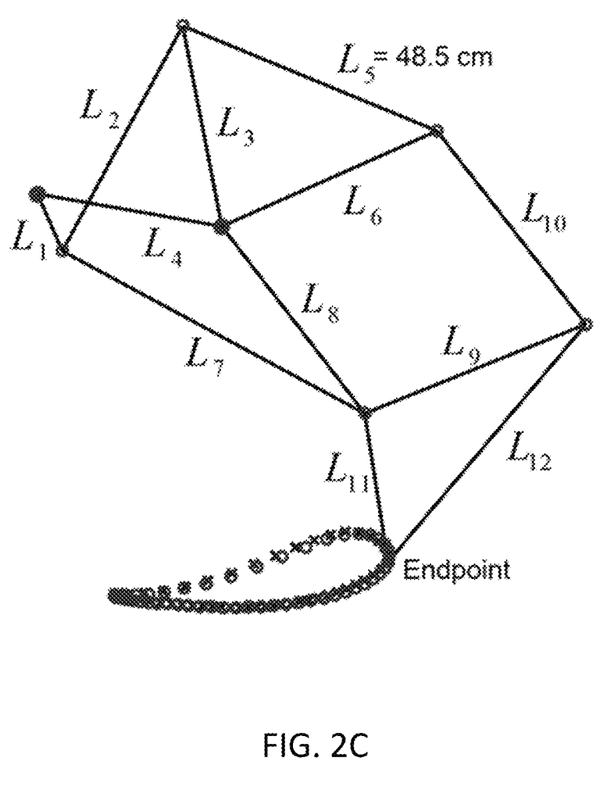
FIG. 2C is a diagram of a first linkage system according to one embodiment.

The sum of trajectory and area differences between the reference meta-trajectory and the end-point of the mechanism within the bounded link lengths can be minimized, starting from the given initial values. Sequential quadratic programming (SQP) can be used to iteratively perform the optimization as it is robust to nonlinearities in the cost function. The SQP approach can be implemented in MATLAB by using the fmincon function in MATLAB R2016A (Mathworks, Inc.). The resulting configuration is shown in FIG. 2C. Optimized to the meta-trajectory, the structure results in an RMS error of 3.09 cm. Blue crosses delineate the meta-trajectory, and red circles show the predicted trajectory.

Figure 3A:
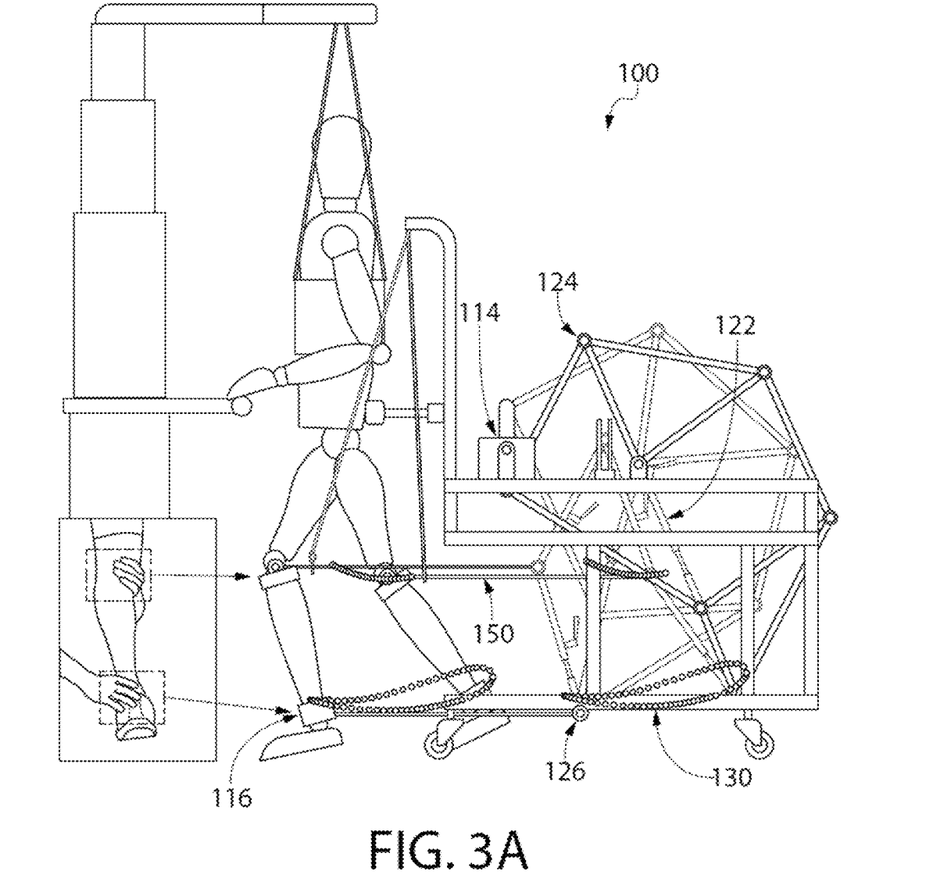
FIG. 3A is a side view and FIG. 3B is a perspective view of a gait training system having extension links according to one embodiment.
Figure 3B:
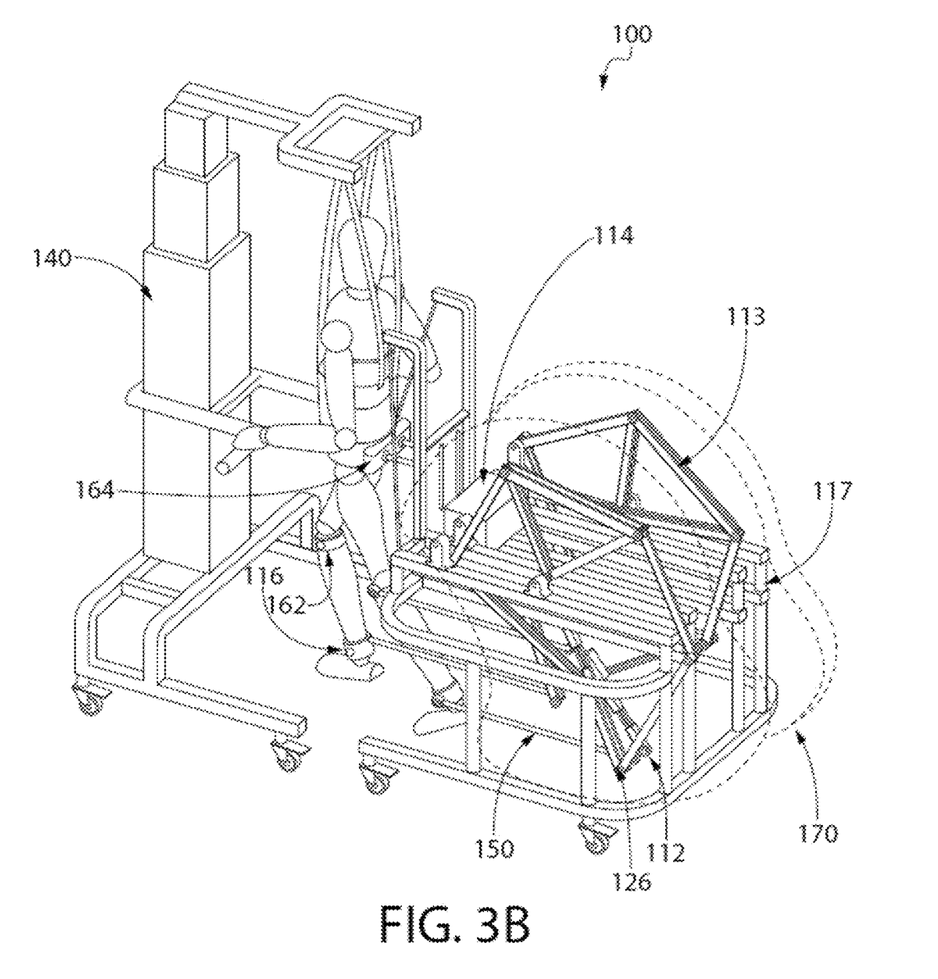

With reference now to FIGS. 3A and 3B, a gait trainer system 100 is shown according to one embodiment. The gait trainer 100 includes a linkage system 112, 113 that is powered by actuator mechanism such as a motor 114 driven belt and pulley system connected to a first 112 and second 113 linkage system. Certain embodiments of the gait trainer 100 may only include a single linkage system 112, such as when the system is only required to be connected to a single ankle. The first linkage system 112 for example includes multiple linkage members 122 connected at a number of rotational joints 124. An endpoint rotational joint 126 is configured to produce a cyclic gait motion 130 when the motor 114 is activated. In one embodiment, the endpoint 126 is located at a bottom joint of the first linkage system 112. In one embodiment, an ankle cuff 116 is attached to the bottom joint 126 via an extension link 150. The extension links 150 provide safe interaction with the therapist by remotely connecting with the patient at the posterior knee and ankle, and providing improved clearance from the rest of the system. A treadmill can be positioned below the linkage systems for the user to walk on, and a body weight support system 140 is connected to a rail 20 disposed above the linkage systems, which can also include a removable pelvic support 164. This approach uses an innovative mechanical design to enable use of a single motor to drive natural, customizable gait patterns (see e.g. FIG. 3A) at knee 162 and ankle 116 cuffs, imitating conventional body weight support gait training. The system can have a height adjustable frame 117 and a cover 170 will house the whole linkage mechanism to prevent potential access to the pinch points during in motion. Interference with the linkage mechanism is further mitigated by separating the user from the linkage mechanism during use via the extension links 150.

Human movements, including walking, possess inherent variability and change with time, gender, age, and body features and even the emotional state. The variations in gait patterns depends on many other parameters, including anthropometric characteristics or gait speeds. In certain embodiments, individual-specific gait pattern estimation is implemented to compensate for these differences in individual patients, and compensation algorithms can be implemented for patients that lose their natural gait motion after injury.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

The approach is to generate gait patterns specific to the participant. Gait patterns can vary widely, mostly influenced by anthropometric characteristics and gait speed. Here, measurements are leveraged and taken from a large database of healthy individuals (113, 63 female) walking at 3.0 km/h on a treadmill to determine the range of gait trajectories that need to be accommodated by the gait trainer.

Figure 4:
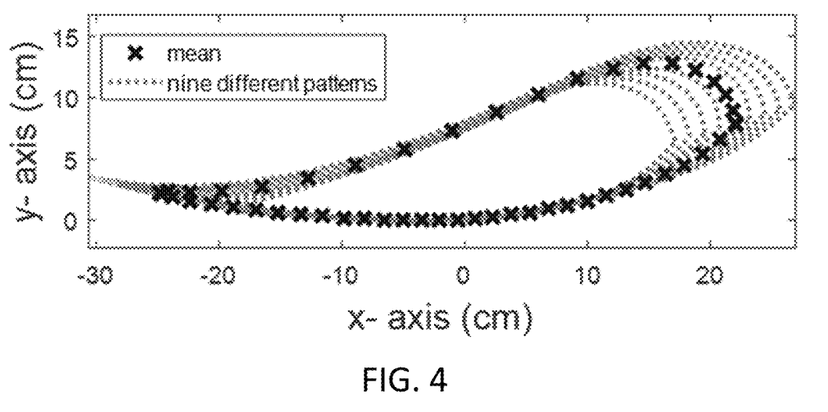
FIG. 4 is a graph illustrating 9 trajectories calculated from a pool of 113 subjects.

The sagittal-plane marker position data of the ankle relative to the pelvis is extracted, separating into single gait cycles based on heel strike. Then those single gait cycle trajectories were normalized into 50 time frames and averaged to represent each subject's gait pattern. From all subjects' gait patterns, the grand mean (called the meta-trajectory) is generated, as well as extracted the mean of the 10 individuals with the largest, average and smallest step lengths to represent the range of gait patterns. As the design of the trainer may have non-linearities, six additional intermediate patterns are interpolated to more thoroughly span the manifold. FIG. 4 illustrates the nine trajectories calculated from the pool of 113 subjects. Mean of total 113 healthy subjects' gait patterns were measured and total 9 gait patterns were identified with different step lengths in the x-y plane (average of 10 subjects for large, medium and small step lengths and their intermediates).

To find the minimum adjustments of the mechanism, these nine canonical gait patterns are used as reference trajectories and then simulated all link adjustment combinations based on the initial optimized configuration to the meta-trajectory. While adjusting all 12 links could flexibly cover the variations in gait patterns the redundancy and impracticality of such adjustments reduce the usefulness of this analysis. Instead, finding the minimum number of link adjustments can facilitate practical use.

Figure 5:
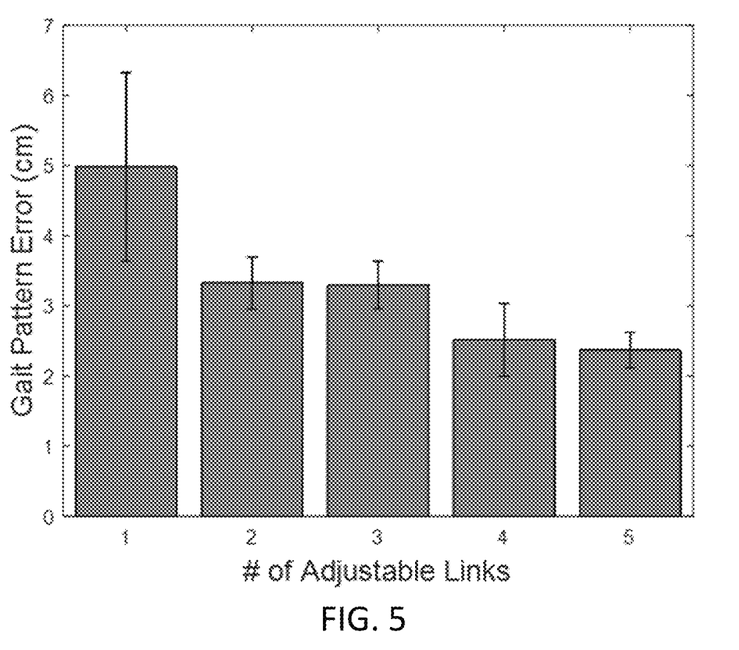
FIG. 5 is a graph of gait pattern error for a number of adjustable links. Adjusting just two links (L4 and L8) provides the largest drop in error for the fewest adjustments.
Figure 6:
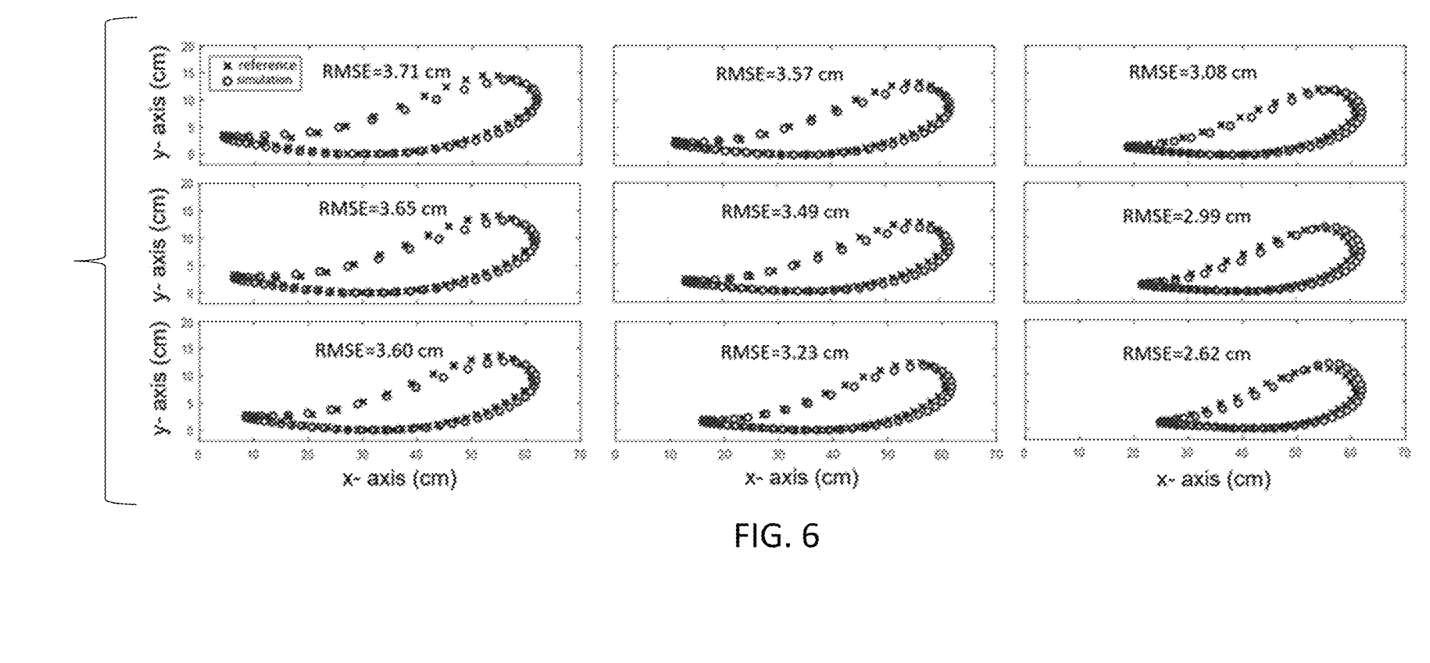
FIG. 6 is a set of graphs illustrating RMS error. The RMS error for each canonical gait pattern given two link adjustments shows consistent performance across patterns, with expectedly larger error in larger gait patterns.

All the combinations among 11 links (except the crank, $L_1$) are selected. For each combination, a set of nine different gait patterns is optimized by using the same cost function in (2). The mean root-mean-square-error (RMSE) of nine patterns is evaluated to evaluate each combination. For each set of adjustable links, the error was defined by the minimum value among the mean RMSE of nine different gait patterns of all combinations. FIG. 5 illustrates the minimum error resulting from one to five link adjustments. Adjusting just two links (L4 and L8) provides the largest drop in error for the fewest adjustments. The results show that the error in adjusting two link lengths ($L_4$ and $L_8$) is not significantly different than adjusting five link lengths. Importantly, the average error of 3.3 cm is under typical within-subject variance of 5.02 cm calculated from the gait database. The trajectory error using two link length adjustments is consistent, ranging from an RSME of 2.62 to 3.71 cm in the canonical gait patterns as shown in FIG. 6. The RMS error for each canonical gait pattern given two link adjustments shows consistent performance across patterns, with expectedly larger error in larger gait patterns.

Figure 7A:
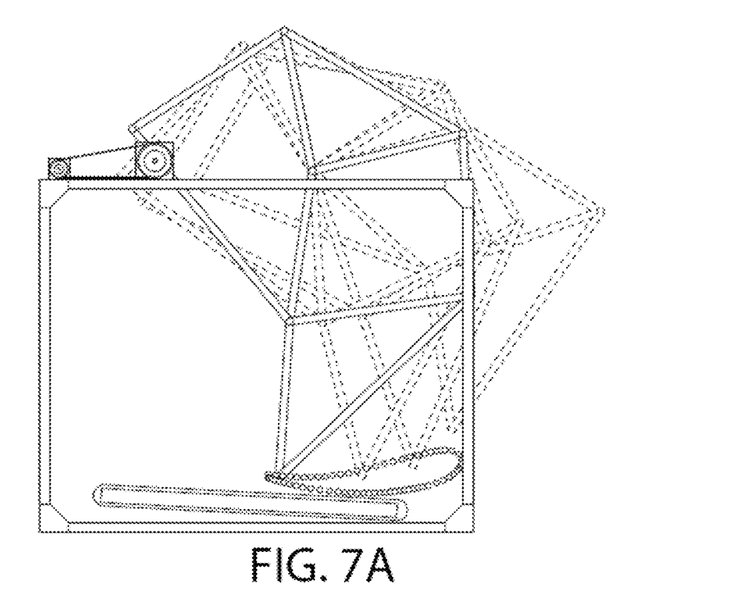
FIG. 7A is an image of a model gait trainer with the range of motion reflecting a natural gait pattern.

To physically validate the gait patterns produced by the simulation, a motorized gait trainer was built as shown in FIG. 7A. Three representative gait patterns of the canonical patterns (smallest, average and largest) were selected and the link lengths were manufactured based on output from the optimization algorithm. A brushless DC servomotor (1.4 kW, Moog Inc.) was used with a gearbox of 5:1 ratio and an additional 2:1 gear reduction though a timing belt drive attached to the output shaft. A motor driver (Moog T200, Moog, Inc.) was used to control the motor. A real-time control system, Simulink Realtime, Matlab (Mathworks) and 16-bit data acquisition system (National Instruments) were used to generate the motor control input at 1 kHz.

A simple impedance based velocity control was achieved with the control input given by $$u = K(\dot{\theta}_{ref} - \dot{\theta}_a) \quad (14)$$

where u is the control input, K is a gain, $\dot{\theta}_{ref}$ is the reference joint velocity input and $\dot{\theta}_a$ is the actual joint velocity of the motor calculated from the encoder. A constant joint velocity was applied at $\pi$ rad/s as the reference control input. The endpoint path in world coordinates was recorded by using an optical motion capture system in 240 Hz (PhaseSpace, Inc.). The optical motion capture data was resampled to calculate the RMSE between the simulated and actual patterns.

Figure 7B:
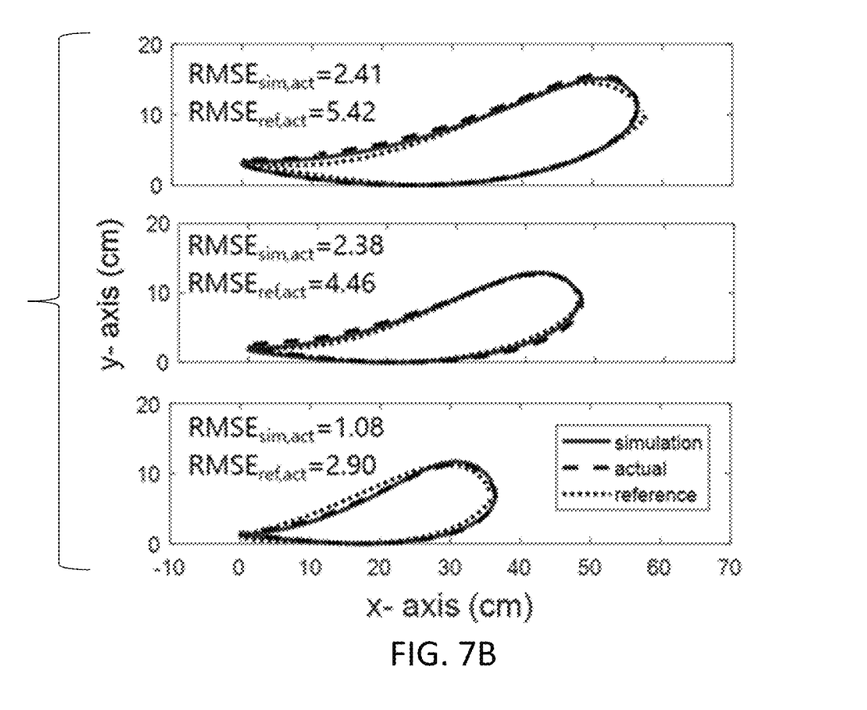
FIG. 7B is a graph of experimental results using an optical motion capture system by adjusting link lengths to match with three different step lengths (largest-top, medium-middle and smallest-bottom).

The performance of the model well-approximated the simulated gait pattern. FIG. 7B illustrates a 2.41 cm RMS error in the largest pattern and a 1.08 cm RMS error in the smallest. Compared to the reference trajectory and based on the canonical gait patterns, the errors translate to 5.42 and 2.90 cm.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A gait training system comprising:
a motor connected to a first linkage system by an actuator; wherein the first linkage system comprises a plurality of linkage members connected to a plurality of joints and a bottom joint that is configured to produce a cyclic gait motion when the motor is activated; wherein the actuator forms a first joint of the plurality of joints and plurality of joints include a second joint; wherein the plurality of linkage members comprise a first linkage member, a second linkage member, a third linkage member, a fourth linkage member, a fifth linkage member, a sixth linkage member, a seventh linkage member, an eighth linkage member, a ninth linkage member, a tenth linkage member and an eleventh linkage member; wherein each of the first, second, third, fourth, fifth, sixth, seventh, eighth, ninth, tenth, and eleventh linkage members comprise a first end and a second end opposing the first end; wherein a first bracket and the first end of the first linkage member form the first joint and the first linkage member is configured to rotate about an axis of the first joint; wherein a second bracket, the second end of the third linkage member, the first end of the fifth linkage member and the first end of the seventh linkage member form the second joint and the third linkage member, the fifth linkage member and the seventh linkage member are configured to rotate about an axis of the second joint; wherein the second end of the first linkage member, the first end of the second linkage member and the first end of the sixth linkage member form a third joint of the plurality of joints and the second linkage member and sixth linkage member are configured to rotate about an axis of the third joint; wherein the second end of the second linkage member, the first end of the third linkage member and the first end of the fourth linkage member form a fourth joint of the plurality of joints and the second linkage member, the third linkage member and the fourth linkage member are configured to rotate about an axis of the fourth joint; wherein the second end of the fourth linkage member, the second end of the fifth linkage member and the first end of the ninth linkage member form a fifth joint of the plurality of joints and the fourth linkage member, the fifth linkage member and the ninth linkage member are configured to rotate about an axis of the fifth joint; wherein the second end of the sixth linkage member, the second end of the seventh linkage member, the first end of the eighth linkage member and the first end of the tenth linkage member form a sixth joint and the sixth linkage member, the seventh linkage member, the eighth linkage member and the tenth linkage member are configured to rotate about a sixth joint; wherein the second end of the eighth linkage member, the second end of the ninth linkage member and the first end of the eleventh linkage member form a seventh joint of the plurality of joints and the eighth linkage member, the ninth linkage member and the eleventh linkage member are configured to rotate about the seventh joint; wherein the second end of the tenth linkage member and the second end of the eleventh linkage member form the bottom joint and the tenth linkage member and eleventh linkage member are configured to rotate about the bottom joint; wherein the first and second bracket are fixed to the frame in the vertical direction and wherein the first and second bracket are slidably adjustable along the frame in the horizontal direction; and wherein an ankle cuff is attached to the bottom joint and the ankle cuff is configured to attach to an ankle of a user to allow the user's leg to move along the cyclic gait motion.

2. The gait training system of claim 1, wherein an endpoint rotational joint is located at the bottom joint of the first linkage system.

3. The gait training system of claim 2, further comprising:
an extension linkage attaching the ankle cuff to the bottom joint.

4. The gait training system of claim 1, wherein the first linkage system comprises a crank mechanism attached to the motor for driving the first linkage system.

5. The gait training system of claim 1, wherein an endpoint rotational joint is configured to produce at least 9 different cyclic gait motions by changing an adjustable length of at least one of the first linkage member, the second linkage member, the third linkage member, the fourth linkage member, the fifth linkage member, the sixth linkage member, the seventh linkage member, the eighth linkage member, the ninth linkage member, the tenth linkage member or the eleventh linkage member of the plurality of linkage members.

6. The gait training system of claim 1, wherein the actuator comprises a drive belt.

7. The gait training system of claim 1, wherein the actuator is connected to a second linkage system.

8. The gait training system of claim 7, further comprising:
a second linkage system comprising eight linkage members connected to a second plurality of joints and a second endpoint rotational joint that is configured to produce a cyclic gait motion 180 degrees out of phase with a first endpoint rotational joint of the first linkage system when the motor is activated.

9. The gait training system of claim 1, further comprising:
a treadmill disposed below the first linkage system.

10. The gait training system of claim 9, further comprising a sensor configured to detect a measure of at least one of user weight or movement and provide a feedback signal to the treadmill for controlling a speed of the treadmill.

11. The gait training system of claim 1, further comprising:
a body weight support system connected to a rail disposed above the first linkage system.

12. A method of customizing a gait pattern on a gait training system comprising:
providing the gait training system of claim 1; and
adjusting a length of at least one of the first linkage member, the second linkage member, the third linkage member, the fourth linkage member, the fifth linkage member, the sixth linkage member, the seventh linkage member, the eighth linkage member, the ninth linkage member, the tenth linkage member or the eleventh linkage member of the plurality of linkage members to correspond with a first gait pattern.

13. The method of claim 12, comprising:
after the step of adjusting, readjusting the length of the at least one of the first linkage member, the second linkage member, the third linkage member, the fourth linkage member, the fifth linkage member, the sixth linkage member, the seventh linkage member, the eighth linkage member, the ninth linkage member, the tenth linkage member or the eleventh linkage member of the plurality of linkage members to correspond with a second gait pattern that is different than the first gait pattern.

* * * * *